United States Patent
Rosner

(10) Patent No.: US 6,683,098 B1
(45) Date of Patent: Jan. 27, 2004

(54) USE OF DRUG MIGLITOL (GLYSET) FOR TREATMENT OF OBESITY TO PREVENT WEIGHT GAIN FOR LOSING WEIGHT AND FOR WEIGHT CONTROL

(76) Inventor: Harvey Rosner, 530F Grand St, Apt. 3F, New York, NY (US) 10002

( * ) Notice: Subject to any disclaimer, the term of this patent is extended or adjusted under 35 U.S.C. 154(b) by 95 days.

(21) Appl. No.: 09/609,847

(22) Filed: Jul. 5, 2000

Related U.S. Application Data

(60) Provisional application No. 60/143,146, filed on Jul. 12, 1999.

(51) Int. Cl.$^7$ ................................................. A61K 31/44
(52) U.S. Cl. ...................................................... 514/343
(58) Field of Search ........................................ 514/343

(56) References Cited

PUBLICATIONS

Debouno et al. The effects of the intestinal glucosidase inhibitor BAY M 1099(Miglitol) on glycemic status of obese–diabetic rats. General Pharmacology, (1993) vol. 24, No. 2, p. 509–515. ISSN: 0306–3623.*

* cited by examiner

Primary Examiner—Theodore J. Criares
Assistant Examiner—Jennifer Kim
(74) Attorney, Agent, or Firm—Muserlian, Lucas and Mercanti

(57) ABSTRACT

A method of affecting weight loss in humans comprising administering to humans in need thereof with a meal of carbohydrate containing food an amount of miglitol sufficient to lower carbohydrate absorption.

3 Claims, No Drawings

USE OF DRUG MIGLITOL (GLYSET) FOR TREATMENT OF OBESITY TO PREVENT WEIGHT GAIN FOR LOSING WEIGHT AND FOR WEIGHT CONTROL

This Application claims benefit of Provisional Application Serial No. 60,143,146 filed Jul. 12, 1999.

BACKGROUND OF THE INVENTION

Miglitol (Glyset) is an oral alpha glucosidase inhibitor. Miglitol acts by a reversible inhibitor of membrane-bound intestinal α-glucoside hydrolase enzymes. Membrane intestinal α-glucosidases hydrolyze oligosaccharides and disaccharides to glucose and other monosaccharides in the brush border of the small intestine. It has minimal inhibitory effect against lactase and would therefore not be expected to induce the symptoms of lactase intolerance. The weight gain or loss for an individual is essentially the difference between the calories absorbed and the calories burned.

Miglitol exerts its effect by blocking the absorption of carbohydrates. The difference between calories digested and the calories excreted (not absorbed due to the action of miglitol) will be the net loss or weight for that particular meal (or lower than expected weight gain). Miglitol does not affect the digestion of proteins or fats. To produce its desired effect, the diet must contain carbohydrate above the monosaccharide level. The use of miglitol represents a major breakthrough in the field of weight control, etc., as listed in the claims by blocking the digestion of ingested carbohydrates. Treatment with miglitol represents a relatively safe method for weight control. The side effects are minimal and are listed in the 2000 Physician's Desk Reference. The use of miglitol for weight control is a much safer method than has been previously used.

BRIEF SUMMARY OF THE INVENTION

The use of miglitol has up to the present time been limited to the treatment of Type II diabetes and is currently marketed under the name Glyset by Pharmacia Corporation. The present invention is the new use of miglitol for weight control. The prevention of weight gain, for weight loss and for the prevention and treatment of obesity. The mechanism of action of miglitol is explained under the Background of the Invention pages. Miglitol is currently marketed under the name Glyset by Pharmacia Corporation in doses of 25 mg., 50 mg. and 100 mg tablets. To exert its effect as per the present invention (new use of known drug miglitol), the drug must be ingested with the meal being consumed. Currently, the drug is by prescription only and dosage will be determined by the prescribing physician and the clinical response of the patient. Dosage will range from 25 mg to 200 mg per ingested meal. The drug may also be administered by incorporation into a wafer or be mixed with certain foods to reduce the amount of carbohydrate absorbed (e.g. in carbohydrate rich foods).

To exert the decided effect in the following claims. The drug miglitol is to be taken with meals and is currently a prescribed drug. The drug will be prescribed by the prescriber depending on clinical response and diet (e.g. the amount of carbohydrate in the diet) (less monosaccharides which are not effected by the action of miglitol). Miglitol will not interfere with the absorption of proteins or fats in the diet.

What is claimed is:

1. A method of affecting weight loss in humans comprising administering to the humans in need thereof with a meal of carbohydrate containing food an amount of miglitol sufficient to lower carbohydrate absorption.

2. The method of claim 1 wherein the human is obese.

3. The method of claim 1 wherein the amount of miglitol is 25 to 200 mg. per meal.

* * * * *